United States Patent [19]

Snyders, Jr.

[11] Patent Number: 5,425,769

[45] Date of Patent: Jun. 20, 1995

[54] COMPOSITION OF MATERIAL FOR OSSEOUS REPAIR

[76] Inventor: Robert V. Snyders, Jr., 645 S. New Ballas Rd.-Apt. No. 1D, St. Louis, Mo. 63141

[21] Appl. No.: 79,795

[22] Filed: Mar. 4, 1993

Related U.S. Application Data

[63] Continuation of Ser. No. 512,379, Apr. 23, 1990, abandoned.

[51] Int. Cl.$^6$ ................................................. A61F 2/28
[52] U.S. Cl. .......................................... 623/16; 623/66
[58] Field of Search .................... 623/16, 11, 12, 8; 427/2; 602/48, 41

[56] References Cited

U.S. PATENT DOCUMENTS

| | | | |
|---|---|---|---|
| 4,279,812 | 7/1981 | Cioca | 604/368 |
| 4,619,655 | 10/1986 | Hanker et al. | 623/16 |
| 4,789,732 | 12/1988 | Urist | 623/16 |
| 4,888,366 | 12/1989 | Chu et al. | 623/16 |
| 4,904,259 | 2/1990 | Itay | 623/16 |
| 5,002,583 | 3/1991 | Pitaro et al. | 623/16 |

Primary Examiner—David Isabella
Attorney, Agent, or Firm—Polster, Lieder, Woodruff & Lucchesi

[57] ABSTRACT

An artificial bone substitute composition consisting of fibrous collagen in a calcium sulfate matrix for incorporation in the human body for ultimate replacement by the body in a metabolic turnover and which can be rendered porous by a foaming agent. Such a composition is adaptable for osseous repair by adjusting the collagen and the calcium sulfate in varying ratios to suit particular applications and including admixtures of growth factors. The composition is prepared in a method of formulating a resorbable material by immobilizing a collagen material having mechanical strength characteristics within a calcium sulfate material and subjecting the composition to a hydration reaction which passes through a fluid state to a moldable state and to a solid.

7 Claims, No Drawings

COMPOSITION OF MATERIAL FOR OSSEOUS REPAIR

This application is a continuation of Ser No. 07/512,379, filed Apr. 23, 1990, now abandoned.

BACKGROUND OF THE INVENTION

1. Field of the Invention

This invention is directed to a biocompatible composition of material to supply artificial parts for overcoming defects in the human body, and for osseous repair.

2. Description of the Prior Art

At present, the most effective ameliorative treatment for osseous repair is autogenous bone grafting, involving the transplantation of bone from another part of a patient's skeleton to the treatment site. Although widely employed, this method has several disadvantages including limited tissue availability and donor site morbidity. Donor site problems in particular discourage wider use of autogenous bone material in elective procedures (e.g., cosmetic bone augmentation, dental implants, periodontal therapy) where the risks to often outweigh potential benefits.

To overcome such problems both allogenic and alloplastic alternatives have been employed. Allogenic (freeze-dried) bone has been utilized with some success, but is expensive and does not heal as well as autogenous bone. Alloplastic ceramics, most notably the calcium phosphates (hydroxylapatite, tricalcium phosphate), have been used quite extensively in bone repair. Employed in both porous and nonporous forms, hydroxylapatite is quite stable in vivo and for all practical purposes, does not resorb. Tricalcium phosphate, while less stable in vivo, still undergoes bioresorption at a very slow rate. While quite appropriate for certain applications (e.g., onlay contouring), this extreme biostability translates into poor working qualities and inhibition of desired bony replacement in other commonly encountered situations.

Attempts to enhance both working qualities and bony replacement in calcium phosphate implants are represented by incorporation of calcium phosphate granules into a binding matrix such as plaster of Paris or collagen. While these adaptations certainly increase workability and encourage bony ingrowth through partial resorption, the phosphate particles will continue to endure and become incorporated in, rather than be replaced by, new host bone. By nature, this introduces planes of weakness into the bony structure which, while acceptable in certain situations, is undesirable in others, and would be preferably avoided where neuromuscular control of bone resorption is not an overriding concern (i.e., onlay contouring). Additional disadvantages include inability of the malleable collagen matrix to attain a solid state in vivo and the resistance of solidifying plaster matrices to molding, as well as the inability of either to be affixed by screw plate attachments.

Recently, the potential to identify and produce sufficient quantities of bone inductive agents has come closer to realization. Concurrently, the concept of delivering osteoprogenitor (pre-bone) cells from either autogenous or recombined sources to desired bone repair sites has developed into a potential repair adjunct. With the development of such biotechnology, hastened bony ingrowth into implants may significantly reduce, if not eliminate the need for composite inclusion of non-resorbable components such as calcium phosphate ceramic.

To this end, the literature has shown the ability of collagen, impregnated with a bone-derived inductive factor, to be transformed into a bony ossicle (complete with marrow cavity) when implanted in vivo, even in sites (such as muscle) where bone would not normally develop. In no case has this same protein been shown to promote bone formation in the absence of an appropriate scaffolding.

Stronger bioresorbable materials, such as ALCAP and polyHEMA are disadvantaged as potential delivery agents for delicate inductive biochemicals because of limitations in workability and the extreme conditions required for their fabrication. Tricalcium phosphate has recently been employed as an experimental delivery agent and found to resorb too slowly to be effective. Even in situations where introduction of inductive agents would not be desired, the necessity of application in precast or granular form still limits utility.

Calcium sulfate hemihydrate ($CaSO_4.5H_2O$) is the dehydrated form of gypsum ($CaSO_4\ H_2O$). It is commonly supplied in powered form of various grades, usually differentiated by dehydration process, purity, and crystal morphology (alpha or beta). Used alone, it is rehydrated into plasters of various densities as determined by the amount of water added over an effective range (density increases with increase in plaster/water ratio; minimum water addition, depending on grade, approximately 20 ml/100 g).

More commonly available as dental plaster, the material is used in a variety of basic and "improved" (more finely and regularly crystallized and combined with mechanical enhancers such as calcium chloride) forms for applications ranging from fabrication of study or prosthetic casts to bite registrations. It is quite similar to plasters used in the building trade.

Collagen is the term applied to a family of fibrous proteins present in all multicellular organisms, subclassified into "Types" (I, II, III, etc.) based upon chemical and functional variations. In its natural state, it is the major fibrous element of skin, tendon, cartilage, blood vessels, and teeth. It is also 95% of the organic content of the bone (bone being 65% mineral and 35% organic) and is simply the most abundant protein in the body.

As a biomaterial, collagen is most frequently available as a reconstituted extract of bovine dermal collagen, although other sources have been used. By various chemical processes, the material is purified and reproduced in a variety of physical forms-sheets, tubes, sponges, powder, fibers, etc.—depending upon the application.

Therefore, the need exists for a rate-variable bioresorbable material which in addition to being easily combinable with advancing biotechnology possesses the inherent mechanical strength to be applied in stress-bearing situations, including an ability to accept plating screws. This material should be capable of resorption as quickly as 3 to 6 weeks if necessary. Additionally, this material should be versatile enough to be introduced as either a liquid, semi-solid or solid; injectable, moldable or pre-cast, while retaining its ability to achieve an acceptable threshold of mechanical strength ex situ or in situ. Such a material would not only reduce the need for use of alloplasts as bone substitutes, but also provide a more workable, utility vehicle in which to deliver them where still required.

Numbered among the many fallen contenders for the position of "more ideal bone substitute" are calcium sulfate and fibrillar collagen, individually. Calcium sulfate has been popular among Orthopedic Surgeons for many years as a biocompatible, quickly resorbable defect filler. Fibrillar collagen has gained some attention as a potential bone substitute recently, coincident to improvements in reconstitution and purification techniques, mainly as an alloplast and biosubstance delivery vehicle.

The alloplastic material with the most potential for meeting those requirements has been Hydroxylapatite (HA), alone or in combination with collagen, plaster or polymer. Synthetic HA [$Ca_{10}(PO4)_6(OH)_2$] is chemically quite similar to the naturally occurring bone HA. It is quite strong, extremely biocompatible and is capable of direct bonding to bone. As a result, HA has become an unqualified commercial success.

But like autologous bone, HA has its deficiencies as well, most notably they are: 1) non-resorbability, and 2) inconvenient handling properties. HA does not actually integrate with bone and hence cannot replace its mechanical properties. Additionally, HA is sometimes associated with dehiscence, extrusion and/or migration of particles. And while recent developments in HA composite technology have diminished some of its shortcomings, it is clear that the ideal bone graft substitute has yet to be found.

BRIEF DESCRIPTION OF THE INVENTION

This invention has as an important object the provision of a prothesis bone structure and a composition of materials therefore designed to loosly mimic the composite structure of human bone by combining a calcium mineral, such as plaster of Paris, with an organic polymer, such as collagen, in a fairly standard volume ratio of approximately 65:35. Alterations in this ratio may be incorporated in order to be able to manipulate specific handling characteristics, depending upon the application desired and materials being carried. Thus, the alterations in ratios are in the range of 7% to 12% collagen on a dry solids basis (d.s.b.).

Another object of the invention is to provide a composition for bone repair which is created by immobilizing a fibrous collagen with a calcium sulfate matrix in a volume ratio of substantially about sixty-five percent calcium sulfate matrix and substantially about thirty-five percent fibrous collagen resulting in a composite material that is resorbable in a desirable time period for the promotion of bony replacement.

Yet another object of the invention is to provide an osteogenic composite material in the presence of bone-derived osteoinductive material, including demineralized bone matrix, bone morphogenetic protein, and phosphophoryn salts.

A further object of the invention is to provide an osteogenic composite material in the presence of growth factors including but not limited to transforming growth factor, fibroblast growth factor and insulin-like growth factor-I.

An object of the invention is manifested in a composition of osteogenic composite materials in combination with certain classes of biochemical agents having positive bone inductive effects to provide a physiologically enhanced scaffolding for bony healing and body contour restoration.

Other objects of the invention will be more fully set forth in the following description thereof.

DETAILED DESCRIPTION OF THE INVENTION

The present invention is a composite combination of the most useful properties of both collagen and plaster which results in the creation of a new biocompatible composite material intended for use in osseous repair, or as a bone graft substitute and substance delivery carrier. The materials being combined are organic collagen and plaster of Paris, referred to herein as composite. The method of effecting the combination of material involves calcification of collagen fibers by mixture with calcium sulfate hemihydrate powder and subsequent mineral rehydration with a water-based liquid. The result is a product which mimics both physical and mechanical characteristics of human bone, which is itself, a composite of calcified collagen fibers. The composite's workability, versatility, and biocompatibility, make it both unique and usable in both the medical and dental arenas.

Collagen may be simply defined as the most abundant protein in the body. It is, in fact, a family of fibrous proteins present in all multicellular organisms. Collagen is the major fibrous element of skin, tendon, cartilage, blood vessels, teeth and is 95% of the organic content of bone (60% mineral 40% organic).

As a biomaterial, collagen has become quite popular in recent years because of its ability to be readily extracted in large quantities from bovine hide. Although obtainable from a variety of other sources, e.g., human placentae bovine tendon porcine dermis, the bovine source is the most abundant most economical and thus most commercially viable. Chemical treatments to purify strengthen and otherwise manipulate the form and function of collagen are well known and available in current literature. Its ability to be produced in a variety of physical forms such as sheets tubes sponges powder and fibers is important in the production of useful medical products. Among these products are hemostatic agents subcutaneous tissue expanders artificial dermis wound dressings, soft tissue augments and ophthalmic shields. As a binder and delivery vehicle reconstitued collagen has been successfully used either clinically experimentally or both in combination with HA and growth factors among other things. It has proven both clinically and experimentally to be quite biocompatible when adequately purified by available methods.

As a biomaterial the advantages of reconstituted collagen include: 1) manipulability of physical characteristics—e.g. morphology, tensile strength; 2) ultimate but rate-alterable resorption; 3) biocompatibility (with proper purification); 4) clinical workability; 5) ability to be combined with and even to chemically bond to other materials. Disadvantages include 1) lack of compressive strength and 2) low-grade allergenicity (1–3%).

What orthopedists have known for many years is that calcium sulfate hemihydrate ($CaSO_4$—$2H_2O$), hereinafter referred to as CS, when rehydrated with sterile water, forms a very safe, very biocompatible bone implant. Traditionally used as a defect filler, this biomaterial is mechanically strong yet totally resorbable over a period of 4–20 weeks, depending upon the type of plaster and degree of hydration. CS not only does not inhibit the normal growth and healing process of bone, it also has been characterized as an accelerant of the same because of its contribution of calcium ions to the process.

Recent advances in CS engineering have made possible a medical grade-calcium sulfate which is completely capable of setting in the presence of blood, whereas earlier calcium sulfate formulations would not set at all in the presence of blood. This advancement actually allows the powder to rehydrate and set even when mixed with blood only. Beyond that, CS may be engineered to set very quickly (within 30 seconds or less) or very slowly (8-10 minutes), depending on the requirements of the application. Furthermore, the concept of introducing three-dimensional (interconnected) porosity into CS mixes has been toyed with previously, and deserves further attention as a means to promote enhanced neovascularization and bony ingress. Resorption rates may be altered as well, by varying the density of the mix within the rehydrating medium—a thick, dense material may facilitate delays in resorption to well beyond the 8 weeks commonly encountered.

In spite of these advances and its inherent versatility, CS alone is still unable to mimic closely enough the mechanical properties of bone. However, I have discovered that CS mixed in certain proportions with reconstituted fibrillar collagen provides the desired properties and requirements of ideal bone substitutes as outlined previously.

Essentially, collagen—plaster composite is intended to mimic bone form and bone mechanics by taking advantage of different properties of two basic materials—just as bone itself does. The "mineralized" collagen fiber network imparts tensile and fatigue strength to the otherwise brittle mineral matrix, while the calcium sulfate provides compressive strength and morphologic stability to the otherwise excessively compliant organic material. No other biocompatible bone graft substitute can claim such structural similarity to human bone, and at the same time offer biocompatibility, resorbability, moldability, workability and versatility.

Following are specific examples of preparation of the composition of this invention.

EXAMPLE I

The composition of the present invention is produced by a method which combines calcium sulphate and collagen in a ratio of substantially 65% calcium sulphate by volume (or 99% to 80% by dry weight) to substantially 35% collagen by volume, or approximately (1% to 20% by dry weight). The calcium sulphate is a high grade crystal (alpha) plaster and the collagen is reconstituted fibrous. The combination takes place in dehydrated status and is mixed to obtain a substantially uniform dispersion before the addition of a hydrate. The hydrate is a 0.9% (normal) saline for rapid in vivo set which produces a mix of medium viscosity at around 40 cc's per 100 grams plaster when used with plaster alone; however, the addition of the hydrophilic collagen requires increasing the hydrate by approximately 5 times the collagen's dry weight.

EXAMPLE II

A variation of the above composition is produced by the method of the addition of an appropriate foaming agent to the hydrate (e.g. cetrimide as 0.25 weight percent of plaster). This introduces a porous character to the composite which is reminiscent of replamine form hydroxylapatite.

It is important that those fabrication guidelines should be considered alterable. By adjusting the fluid volume, material ratios, preparation conditions, and additives, this composition may be tailored to a variety of applications, such as precast, moldable, or injectable alone or as a delivery vehicle; accelerated or retarded set; accelerated or retarded bioresorption. No one formulation will suffice in every situation; therefore a range of formulations is essential for any useful bone substitute, including bone itself.

In a general consideration, the compositions may be created so it can be applied to precasting, or to a moldable state, or to a fluid state suitable for applications by injection. The hydrate to have for the composition of 65:35 calcium sulphate to collagen is a normal 0.9% saline. The castable or thick composition at 65:35 ratio results from hydrate of from 25 to 35 cc per 100 grams, while the thin composition at 65:35 ratio is obtained with approximately 35 to 50 cc per 100 grams.

TABLE I—VARIABLES

When a range of characteristics needs to be considered which will affect the biological and mechanical factors, the behavior of the calcium sulphate—collagen admixture can be varied according to the following table:

| Factor | Increase | Decrease |
| --- | --- | --- |
| Setting Time | Add citric acid | Saline salts |
|  | Borax | Ground set plaster |
|  | Cold hydrate | Warm hydrate |
|  | More hydrate | Less hydrate |
|  | More collagen | Less hydrate |
| Density | Less hydrate | More hydrate |
|  | Regular plaster crystals | Irregular plaster crystals |
|  | Less collagen | More collagen |
| Resorption Rate | Decrease density | Crosslinked Collagen Cyanoacrylate |
| Tensile Strength | More collagen | Less collagen |
|  | More collagen crosslinks | Less collagen crosslinks |
| Compressive Strength | More plaster | Less plaster |
|  | Less hydrate | More hydrate |
| Viscosity | Less hydrate | More hydrate |
|  | More collagen | Less collagen |

With an appreciation for the composite's convenient handling properties, bone-like physical properties, range of formulations and resorption characteristics, it has immense potential as a carrier vehicle for a variety of particulate alloplastic (e.g., bioglasses, calcium phosphates, methacrylates) allogenous (freeze-dried bone chips) and autologous materials (bone marrow, bone paste, bone chips), or as a mortar in conjunction with blocks of the same.

The most important aspect of the composite's combinability, however, may well lie in its potential to simultaneously incorporate and deliver biochemical agents; particularly, the so-called "bone-inductive proteins".

For many years, it has been known that bone contains biochemical factors which are released and/or activated in response to bone injury See M. R. Urist, Science, 150, 893-1965), and that these factors are essential not only in fracture repair but bone graft repair as well. Following the discovery that demineralized, lyophilized bone (demineralized bone matrix) possessed osteoinductive qualities, researchers have been able to demonstrate consistently that purified protein extracts of this matrix (variously known as bone morphogenetic protein, osteogenin, osteoinductive factor, etc. . . . ) are capable of regenerating complete bony ossicles (vascularized, marrow-containing, functional bone units) within a matter of weeks. Although widespread use of bone-inductive proteins has been prohibited because of its presence in very minute quantities in human bone, the current availability of highly purified bovine extracts and potential availability of recombinant genetic analogs has intensified the search for an appropriate carrier vehicle.

Without an appropriate carrier vehicle, bioactive induction agents are ineffective. Experimentally, fibrous collagen has served most commonly in this capacity, preventing excessively rapid resorption/diffusion of the proteins and providing an attachment matrix for inductive cell ingrowth. Even when implanted in soft tissue, collagen impregnated with a bone-inductive protein has been shown to regenerate bony ossicles as morphological duplicates of original implants. Nevertheless, researchers have consistently acknowledged that a stronger, more versatile carrier material will be required for the rigors of clinical application.

The qualities required in a bone-inductive carrier material (in essence, a "synthetic bone") have been outlined to be mechanically strong, yet capable of bioresorption within a matter of weeks. It must be biocompatible, possess convenient handling properties, and be tailorable to fit the particular needs of each type of osseous repair site. The family of compositions contained within the scope of this invention are quite applicable to the above description and the use to which it refers.

It is important to note that in addition to the specific osteoinductive factors identified previously, a series of bone-derived and non-bone growth factors have also been described as having either primary or synergistic roles in bone repair. These include, but are not limited to: PDGF, TGF, FGF, and IGF-1. These growth factors promote bone repair by direct effects on bone precursor cells, indirect effects on essential bone repair support mechanisms such as capillary invasion, or both. Furthermore, certain biochemical agents which are neither "growth factors" nor "inductive factors" per se have been shown to promote bone repair as well. These include, but are not limited to: dihydroxyvitamin-$D_3$, prostaglandin $E_1$, and interleukin-1.

All of these materials may conceivably be carried by the composite, alone or in combination, with or without alloplastic, allogenic, autogenic or other materials in tow. Methods for immobilization in collagen alone have been presented in the literature, however, plaster has been shown to act as a predictable carrier for biochemical agents by simple mix incorporation. Furthermore, it is possible to incorporate other carrier forms (e.g., biodegradeable polylactic/polyglycolic acid capsules) within the matrix of this invention. Any of these methods may be deemed useful within the scope of this invention, though in the spirit of simplicity, plaster incorporation is to be considered most efficient unless specifically contraindicated.

Given the complex cascade of biochemical elements involved in bone repair, it is likely that these various agents will prove to be most effective in some yet-to-be-determined variety of combinations, with different combinations indicated for different osseous repair situations. Nevertheless, it is imperative that an effective delivery matrix be devised for use with both currently available and future biochemical bone repair technology.

In situations where it is deemed useful to deliver alloplastic materials such as HA within the matrix of the composite, specific materials ratios must be determined by the surgeon according to the specific nature of the osseous repair. If greater malleability is desired, plaster percentage may be decreased at the expense of ultimate compressive strength, shape preservation and calcium ion concentration during the repair process. If maintenance of a specific contour and strength, or the presence of flow characteristics are determined to be more important, collagen percentage may be decreased accordingly. The reduction of percent plaster to less than 40% volume in any useful collagen:alloplast ratio will significantly retard setting time and strength, particularly if set is expected to take place in a wet environment, although there may be instances where such a mix might still prove useful. Nevertheless, the most useful volume ratios of plaster:collagen for carrying bioresistant alloplasts will be 75:25 (by volume) or greater. Alloplasts may then be included in amounts up to 35–40% of plaster weight.

The inclusion of "dry" autogenic or allogenic bone particles within the matrix of the composite may be governed by similar considerations, provided the particles are below a certain critical size parameter. Though not specifically determined, it is safe to say that 1) the greater the percentage of bone included, the smaller the particles must be; and 2) particulate bone included above 50% volume levels would be excessively disruptive of the composite matrix no matter how small the particles.

The inclusion of bone marrow or "wet" autogenic material within the composite must be governed by the understanding that blood may significantly affect plaster set within the matrix. Although the more highly refined plasters perform better in the presence of blood, all suffer from at least some increase in setting time. As new techniques of marrow cell isolation and purification develop, these materials will be capable of inclusion at percentages comparable to other allo- and autoplasts. Otherwise, these "wet" autogenous materials will still be quite capable of delivery within the composite vehicle, but at reduced levels (probably in the range of 10–15% at most). In the long run, this may prove to be adequate anyhow, particularly in the presence of included bioactive agents.

Additional uses of the composite as a carrier vehicle may employ a wide variety of therapeutic agents ranging from antibiotics to electrically charged granules. Antibiotics for local delivery would be directly incorporated by mixing, or delivered within an additional biodegradeable matrix, for release over a specified period of time. Low-grade electrical charge has been shown to be a stimulus to both fibrous and hard tissue proliferation, and could be used to advantage when delivered alone or in combination with other materials or inductive agents, as governed by the general rules of combinability discussed above.

Ultimately, the most useful plaster:collagen ratios will be determined by the bone growth efficacy of the biochemical agents the composite delivers and the nature of the various particular sites of osseous repair. The composite is offered as an essential bridge between laboratory and clinical bone repair, versatile enough to be tailored to the varying and unique needs of both. It may be applied in a great variety of clinical situations, as evidenced in the following examples:

CLINICAL EXAMPLE I

A patient develops a large pathological bone cyst of the body of the mandible, which must be surgically removed. Left with a large defect comprising both structure and esthetics, the surgeon is faced with the need to pack the defect with large amounts of iliac crest (hip) bone harvested during a second procedure. As an alternative, the surgeon may use the composite as a bone graft extender, thus reducing the amount of bone required and the size of the donor site. Furthermore, the composite acts as a mortar to both immobilize bone and recontour the defect site according to original morphology, in addition to much needed structural support. With the inclusion of proven bone growth promotors in the composite, the need for hip bone could be further reduced to either a less invasive marrow harvest or eliminated altogether. Any additional support required for the defect fill may be provided with resorbable plating systems. Within a short period of time, the bone repair material is resorbed and replaced with the patient's own bone.

CLINICAL EXAMPLE II

A patient has four lower teeth extracted, necessitating fabrication of a dental prosthesis. The patient prefers to have osseointegrated dental prostheses implanted for final reconstructions, as indicated in that case. Faced with a six-month healing period prior to implantation of the submergible root portions of the implants, after which another 6 months to one year must pass prior to attachment of the oral portion of the prostheses, the surgeon elects to place implants immediately into the extraction sockets. After shaping the socket appropriately and establishment of acceptable hemostasis, the implant is placed into the site and composite poured/packed around it as both a splint and bone repair agent, and tissue closed over it. 6 months later (less with the inclusion of an appropriate biochemical bone repair agent), the superior portions of the implants are uncovered and the oral attachments affixed. The same approach may be used when creating new implantation sites within solid bone, and may prove particularly useful in maxillary sites to "prop up" an encroaching sinus and provide adequate bone depth to support the artificial root.

Also, the emplacement of root prostheses alone, for the purpose of edentulous ridge preservation may benefit by similar approaches.

Not only does the successful use of this approach render the implant procedures technically less difficult, but it may also permit some redesigning of implants currently limited to apical convergence or at most, parallelism. By permitting apical divergence and/or undercutting, it may be possible to create implants more favorable to stress distribution, retention, or both.

CLINICAL EXAMPLE III

A patient exhibiting maxillary hypoplasia is treated with orthognathic surgery to move the maxilla downward and forward. Instead of block bone grafts from the hip, precast slabs of composite are wedged as interpositional grafts into interbony spaces created by the intended displacement. To further stabilize the wedges, fresh composite paste is used as a mortar between the precast material and the bone.

The wedges could be predesigned to match projected gaps, and would carry inductive biochemical agents and/or alloplastic materials as necessary. If inclusion of autogenous marrow was deemed useful, that too, could be accomplished by addition to the precast and/or fresh material.

Similar modes of treatment would be employed for genioplasties, mandibular advancements, or other procedures where interpositional grafts are useful.

CLINICAL EXAMPLE IV

A patient presents for surgical augmentation of a deficient area on the forehead. After suitable access and hemostasis are obtained, a thick, malleable mix of composite and a particulate calcium phosphate alloplast (hydroxylapatite) are mixed and then molded into place over the frontal bone. After the material has been shaped appropriately, it is allowed to set before closure.

Given the addition of a suitable biochemical bone induction agent, it is expected that such a procedure could be successfully performed without delivering any bioresistant alloplasts at all—that is, within several weeks, the entire composite onlay mold would be replaced with the patient's own induced, ingrown bone.

These clinical examples represent just a few of the many uses possible for this material.

What is claimed is:

1. A biocompatible and bioresorbable bone substitute consisting of collagen fibers distributed within a matrix of calcium sulfate dihydrate $CaSO_4$—$2H_2O$, said bone substitute having physical and chemical properties of bone, wherein said bone substitute is molded in situ from a pliable phase to a solid phase when implanted in a host.

2. The artificial bone substitute set forth in claim 1 wherein said composition of collagen fibers distributed within said matrix of calcium sulfate dihydrate is combined in a weight ratio of substantially 99 to 80 percent matrix and 1 to 20 percent collagen.

3. The artificial bone substitute set forth in claim 1 wherein said composition has immobilized collagen fibers within a calcium sulfate dihydrate matrix in a volume ratio of substantially about sixty-five percent calcium sulfate matrix and substantially about thirty-five percent collagen resulting in a material that is capable of bioresorption in a time period coincident to host bone ingrowth and replacement.

4. The artificial bone substitute set forth in claim 1 wherein said composition is physically moldable and allows for contouring and filling osseous defects to promote bony replacement.

5. The artificial bone substitute set forth in claim 1 wherein said composition is admixed with a class of non-collagenous bone-derived proteins which include bone morphogenetic protein, ostercalcin, or osteogenin.

6. The artificial bone substitute set forth in claim 1 wherein said composition is an admixture of a class of non-bone derived proteins which include transforming growth factors or insulin-like growth factors or fibroblast growth factors.

7. The artificial bone substitute set forth in claim 1 wherein a fibrous collagen with a calcium sulfate matrix is porous and disposed to become incorporated by the human body as part of human tissue for ultimate replacement by the body in a substantial metabolic turnover.

* * * * *